(12) United States Patent
Ahn et al.

(10) Patent No.: US 9,980,682 B2
(45) Date of Patent: May 29, 2018

(54) CURVED MOVABLE BEAM STOP ARRAY AND CBCT COMPRISING THEREOF

(71) Applicants: GIL MEDICAL CENTER, Incheon (KR); GACHON UNIVERSITY OF INDUSTRY-ACADEMIC COOPERATION FOUNDATION, Gyeonggi-do (KR)

(72) Inventors: So Hyun Ahn, Gyeonggi-do (KR); Kyu Chan Lee, Gyeonggi-do (KR)

(73) Assignees: GIL MEDICAL CENTER, Incheon (KR); GACHON UNIVERSITY OF INDUSTRY-ACADEMIC COOPERATION FOUNDATION, Gyeonggi-do (KR)

( * ) Notice: Subject to any disclaimer, the term of this patent is extended or adjusted under 35 U.S.C. 154(b) by 0 days. days.

(21) Appl. No.: 14/411,880

(22) PCT Filed: Sep. 30, 2014

(86) PCT No.: PCT/KR2014/009161
§ 371 (c)(1),
(2) Date: Dec. 29, 2014

(87) PCT Pub. No.: WO2016/003016
PCT Pub. Date: Jan. 7, 2016

(65) Prior Publication Data
US 2017/0105684 A1    Apr. 20, 2017

(30) Foreign Application Priority Data
Jul. 2, 2014 (KR) .................. 10-2014-0082669

(51) Int. Cl.
*A61B 6/03* (2006.01)
*A61B 6/04* (2006.01)
(Continued)

(52) U.S. Cl.
CPC ............ *A61B 6/032* (2013.01); *A61B 6/0407* (2013.01); *A61B 6/06* (2013.01); *A61B 6/14* (2013.01);
(Continued)

(58) Field of Classification Search
CPC ......... A61B 6/032; A61B 6/06; A61B 6/4035; A61B 6/4085; A61B 6/4435; A61B 6/54;
(Continued)

(56) References Cited

U.S. PATENT DOCUMENTS 5,550,886 A * 8/1996 Dobbs .................... A61B 6/032
378/19
5,608,776 A * 3/1997 Hsieh ...................... G21K 1/04
378/145
(Continued)

FOREIGN PATENT DOCUMENTS

| JP | 2012112882 | 6/2014 |
|---|---|---|
| KR | 1020120138451 | 12/2012 |
| KR | 10-2014-0039353 | 4/2014 |

OTHER PUBLICATIONS

Office Action dated Jul. 24, 2015 for Corresponding KR Application 10-2014-0082669.
(Continued)

*Primary Examiner* — Allen C. Ho
(74) *Attorney, Agent, or Firm* — Gottlieb, Rackman & Reisman, P.C.

(57) ABSTRACT

A curved movable beam-stop array which has a generator, a curved grid and a controller. The generator generates radiation beams while rotating to a gantry angle. The curved grid is positioned in the radiation direction of the radiation beams generated from the generator. The controller controls operations of the grid. A plurality of slits of the grid are spaced apart from each other at a predetermined distance and allow
(Continued)

at least a portion of the radiation beams generated from the generator to pass through. The controller moves the slit by a predetermined distance when the generator moves by a predefined angle.

10 Claims, 7 Drawing Sheets (51) Int. Cl.
G21K 1/02 (2006.01)
G21K 1/04 (2006.01)
A61B 6/00 (2006.01)
A61B 6/14 (2006.01)
A61B 6/06 (2006.01)

(52) U.S. Cl.
CPC .......... *A61B 6/4035* (2013.01); *A61B 6/4085* (2013.01); *A61B 6/4435* (2013.01); *A61B 6/54* (2013.01); *A61B 6/542* (2013.01); *G21K 1/02* (2013.01); *G21K 1/025* (2013.01); *G21K 1/04* (2013.01); *G21K 1/043* (2013.01); *G21K 1/046* (2013.01)

(58) Field of Classification Search
CPC .......... A61B 6/542; G21K 1/02; G21K 1/025; G21K 1/04; G21K 1/043; G21K 1/046
USPC ............................................. 378/16, 147–153
See application file for complete search history.

(56) References Cited

U.S. PATENT DOCUMENTS

| | | | | |
|---|---|---|---|---|
| 5,864,597 | A * | 1/1999 | Kobayashi | A61B 6/027 378/15 |
| 5,949,811 | A * | 9/1999 | Baba | A61B 6/4225 378/108 |
| 5,999,587 | A * | 12/1999 | Ning | A61B 6/4447 378/4 |
| 6,125,167 | A * | 9/2000 | Morgan | H01J 35/10 378/121 |
| 6,229,870 | B1 * | 5/2001 | Morgan | A61B 6/032 378/4 |
| 6,396,902 | B2 * | 5/2002 | Tybinkowski | G21K 1/025 378/148 |
| 6,445,761 | B1 * | 9/2002 | Miyazaki | A61B 6/032 378/16 |
| 6,459,770 | B1 * | 10/2002 | Tybinkowski | A61B 6/06 378/147 |
| 7,076,019 | B2 * | 7/2006 | Hagiwara | A61B 6/032 378/16 |
| 7,113,569 | B2 * | 9/2006 | Okumura | A61B 6/032 378/150 |
| 7,170,975 | B2 * | 1/2007 | Distler | A61B 6/032 378/147 |
| 7,190,758 | B2 * | 3/2007 | Hagiwara | A61B 6/032 378/7 |
| 7,194,061 | B2 * | 3/2007 | Fujita | A61B 6/032 378/150 |
| 7,209,547 | B2 * | 4/2007 | Baier | A61B 6/032 378/148 |
| 7,260,171 | B1 | 8/2007 | Arenson | |
| 7,289,596 | B2 * | 10/2007 | Horiuchi | G01N 23/046 378/4 |
| 7,313,216 | B2 * | 12/2007 | Nishide | A61B 6/032 378/15 |
| 7,409,034 | B2 * | 8/2008 | Gohno | A61B 6/032 378/15 |
| 7,486,773 | B2 | 2/2009 | Maltz et al. | |
| 7,508,903 | B2 * | 3/2009 | Nishide | A61B 6/06 378/15 |
| 7,583,775 | B2 * | 9/2009 | Ozaki | G21K 1/04 250/370.11 |
| 7,706,500 | B2 * | 4/2010 | Kondo | A61B 6/032 378/15 |
| 7,957,507 | B2 * | 6/2011 | Cadman | A61N 5/1042 378/153 |
| 8,005,187 | B2 * | 8/2011 | Suzuki | A61B 6/032 378/19 |
| 8,009,794 | B2 * | 8/2011 | Partain | A61B 6/032 378/150 |
| 8,064,568 | B2 * | 11/2011 | Von Der Haar | A61B 6/032 378/147 |
| 8,094,775 | B2 * | 1/2012 | Noshi | A61B 6/032 378/15 |
| 8,094,785 | B2 * | 1/2012 | Heid | G21K 1/04 378/149 |
| 8,213,568 | B2 | 7/2012 | Heuscher | |
| 8,571,172 | B2 * | 10/2013 | Dafni | A61B 6/032 378/11 |
| 8,693,621 | B2 * | 4/2014 | Thran | A61B 6/4447 378/17 |
| 8,712,138 | B2 * | 4/2014 | Gleich | A61B 6/4241 382/132 |
| 8,897,413 | B2 * | 11/2014 | Heuscher | A61B 6/032 378/15 |
| 8,989,348 | B2 * | 3/2015 | Cox | G01N 23/04 378/146 |
| 9,014,341 | B2 * | 4/2015 | Zhang | A61B 6/03 378/147 |
| 9,036,775 | B2 * | 5/2015 | Yoshikawa | A61B 6/145 378/38 |
| 9,036,776 | B2 * | 5/2015 | Sadakane | A61B 6/145 378/38 |
| 9,121,809 | B2 * | 9/2015 | Cox | G01N 23/04 |
| 9,125,572 | B2 * | 9/2015 | Noo | A61B 6/027 |
| 9,144,408 | B2 * | 9/2015 | Shahar | A61B 6/037 |
| 9,204,852 | B2 * | 12/2015 | Edic | A61B 6/482 |
| 9,208,918 | B2 * | 12/2015 | Tybinkowski | G21K 1/02 |
| 9,230,701 | B2 * | 1/2016 | Teng | G21K 1/02 |
| 9,237,875 | B2 * | 1/2016 | Pan | A61B 6/06 |
| 9,263,160 | B2 * | 2/2016 | Kang | G21K 1/025 |
| 9,295,434 | B2 * | 3/2016 | Herold | A61B 6/032 |
| 9,312,038 | B2 * | 4/2016 | Takagaki | A61B 6/06 |
| 9,332,946 | B2 * | 5/2016 | Heuscher | A61B 6/032 |
| 9,357,971 | B2 * | 6/2016 | Yoshikawa | A61B 6/032 |
| 2008/0237473 | A1 | 10/2008 | Uribe | |
| 2008/0317212 | A1 | 12/2008 | Kuehn | |
| 2010/0254508 | A1 | 10/2010 | Von Der Haar | |
| 2012/0134472 | A1 | 5/2012 | Kaneko | |
| 2014/0086380 | A1 | 3/2014 | Song | |
| 2014/0270091 | A1 * | 9/2014 | Nemeth | G21K 1/043 378/150 |

OTHER PUBLICATIONS

So Hyun Ahn et al; "Development of a Beam Stop Array System with Dual Scan Mode for Scatter Correction of Cone-beam CT"; Journal of the Korean Physical Society, vol. 64, No. 8, Apr. 2014, pp. 1220-1229; Incheon, Korea.

Office Action Issued by the Australian Government IP Office for corresponding application No. 2014-280988 dated Dec. 31, 2014.

* cited by examiner

CURVED MOVABLE BEAM STOP ARRAY AND CBCT COMPRISING THEREOF

CROSS-REFERENCE TO RELATED APPLICATIONS

This patent application claims the benefit under 35 U.S.C. § 371 PCT/KR2014/009161, filed Sep. 30, 2014, which claims priority to Korean Patent Application No. 10-2014-0082669, filed Jul. 2, 2014, both of which are hereby incorporated by reference as part of the present disclosure.

FIELD OF THE INVENTION

The present invention relates to a beam-stop array (BSA) that is curved and moveable, and more particularly to a beam-stop array that is curved and moveable and which can be applied to accurately and efficiently improve the quality of images of a cone-beam computerized tomography (CBCT) system, and particularly, can be applied to not only a simulation cone-beam computerized tomography system necessary for radiotherapy and a cone-beam computerized tomography system mounted in a radiotherapy apparatus, but also a wide range of fields including plastic surgery, maxillofacial surgery, dental surgery, and the like.

BACKGROUND OF THE INVENTION

Unlike an existing computerized tomography (CT) apparatus, a cone-beam computerized tomography system takes images while moving to a predefined angle about an object so that the three-dimensional (3D) and four-dimensional (4D) imaging of an object to be examined is possible, thereby obtaining three-dimensional anatomical information. Further, unlike MRI, the cone-beam CT system more easily takes images of hard tissue, such as bone, rather than soft tissue, such as muscular tissue. The cone-beam computerized tomography system is variously applied in medical treatment or convalescence as well as in the diagnosis of diseases.

However, since the X-ray beams of the cone-beam computerized tomography system irradiate a wide area, photons of the X-ray beams that have a reduced energy of 100 keV or less are scattered by the object to be examined and so a low spatial frequency is obtained. Therefore, when the X-ray beam reaches a sensing device, due to not being able to distinguish the scattered X-ray beam from the primary X-ray beam in the original state, an image which is partially indefinite with considerably inferior quality is obtained as a result.

The photographing of images is accompanied by phenomena such as degradation of contrast, increase in noise and inaccuracy of computerized tomography values. Hence, a process of analyzing and correcting the degree of scatter (scatter correction) is required in order to obtain a definite image.

Among several methods for scatter correction, beam-stop array method is known as an effective method. A beam-stop array partially intercepts scattered beams, so that it is possible to estimate and correct the distribution of the scattered beams. However, several problems still exist in the beam-stop array.

Particularly, there is a problem in that conventionally, additional scans are required to correct the distribution of scattered beams, and therefore, increasing the amount of scattered beams absorbed in an object to be examined. In order to overcome this problem, Korean Patent Publication No. 10-2012-0138451 discloses a system and apparatus for circularly scanning an object to be examined using a scatter image correcting device, performing one-dimensional scatter correction by detecting X-ray projection image data using a multi-line X-ray detector, obtaining a scatter correction projection image by removing estimation scatter image data obtained through the one-dimensional scatter correction, and restoring an image using a back-projection filtration method based on the obtained scatter correction projection image.

However, although the number of additional scans can be reduced using the system and apparatus, generally, a penumbra is produced at the edges of strip lattices that intercept the beams. In this case, there still exist problems difficult to overcome using the back-projection filtration method provided in the invention described above.

When radiation acts on an object, the penumbra is differentiated from the isodose area which evenly receives a certain amount of radioactivity, whereas the penumbra means an area that receives only 20% to 80% of the radioactivity. Therefore, valid data that may be obtained from the empty space portion is contaminated. As a result, there remains a problem in that an indefinite image is obtained. For this problem, the invention provides a method of forming the width of the strip lattices so as to be narrower than that of the empty space portions. However, there is a limitation in suppressing the formation of a penumbra by forming the width of the strip lattices to be narrow. Particularly, when photographing is performed throughout a wide area such as the chest and abdomen of a person, a penumbra still forms, and therefore, loss of image information occurs in the area of the penumbra. As a result, the image obtained differs from the actual object.

U.S. Pat. No. 7,486,773 discloses a method of estimating the degree of scatter of beams irradiated using a plurality of cone-shaped members rather than strip lattices. As such, the use of a plurality of members can reduce error during the process of estimating the degree of scatter of beams even when photographing is performed throughout a wide area. However, the degree of scatter is estimated using at least four images obtained by photographing four times. Therefore, an increase in the amount of radioactivity absorbed in the object to be examined may occur, along with an increase in the time required to photograph.

SUMMARY OF THE INVENTION

Therefore, an aspect of the detailed description is to provide a system which can reduce the amount of radioactivity absorbed by the object to be examined and decrease the time required to take the images.

Another aspect of the detailed description is to provide a beam-stop array that is able to perform photographing of a wide area and at the same time lessen the penumbra effect.

Still another aspect of the detailed description is to provide a differentiated beam-stop array for obtaining more precise and definite images by reducing the error in estimating the degree of scatter.

To achieve these and other advantages and in accordance with the purpose of this specification, as embodied and broadly described herein, a beam-stop array comprises a generator configured to generate radiation beams while rotating to a gantry angle; a curved grid positioned in the direction of the radiation beams generated from the generator; and a controller configured to control operations of the grid, wherein the grid comprises a plurality of slits spaced apart from each other at a predetermined distance, the plurality of slits allowing at least a portion of the radiation beams generated from the generator to pass therethrough, and wherein the controller moves the slits by a predetermined distance d when the generator moves by a predefined angle α.

The beam-stop array may further comprise a flat panel detector disposed facing the generator. The grid may be positioned between the flat panel detector and the generator.

The generator and the grid may rotate about rotation axis. The grid may be positioned between the generator and a table, and the slit may be positioned perpendicular to the rotation axis.

The grid may be curved convexly towards the table.

The grid may further comprise a beam-stop unit which blocks radiation beams, being alternately disposed with said slits.

The beam-stop unit may comprise a movable spaced unit.

The controller may further comprise a spacing control means configured to control the movement of the spaced unit.

The spaced unit may be formed with a plurality of spaced units to stop at least a portion of respective said slits.

The ratio of the spacing of the slits to the thickness of the beam-stop unit may be 1.0.

To achieve these and other advantages and in accordance with the purpose of this specification, as embodied and broadly described herein, a cone-beam computerized tomography system comprising the a beam-stop array is provided.

As described above, according to the present invention, a definite image can be obtained through just one scan, so it is possible to reduce the amount of radioactivity absorbed in an object to be examined. Thus, it is possible to reduce radiation dose and to decrease the time required to take the images.

Further, the curved movable grid can perform taking images of a wide area and at the same time lessen the penumbra effect.

Further, as X-ray beams are irradiated while rotating around an object, the grid moves at a predetermined space, which in turn reduces the error in estimating scatter distribution of an image, and thereby more accurate and definite images may be obtained.

Further scope of applicability of the present application will become more apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from the detailed description.

BRIEF DESCRIPTION OF THE DRAWING

The accompanying drawings, which are included to provide a further understanding of the invention and are incorporated in and constitute a part of this specification, illustrate exemplary embodiments and together with the description serve to explain the principles of the invention. In the drawings.

DETAILED DESCRIPTION OF EXEMPLARY EMBODIMENTS

Hereinafter reference will now be made in detail to various embodiments of the present invention, examples of which are illustrated in the accompanying drawings and described below. While the invention will be described in conjunction with exemplary embodiments, it will be understood that present description is not intended to limit the invention to those exemplary embodiments. On the contrary, the invention is intended to cover not only the exemplary embodiments, but also various alternatives, modifications, equivalents and other embodiments, which may be included within the spirit and scope of the invention as defined by the appended claims.

In the present invention, a cone-beam computerized tomography system comprising a curved movable beam-stop array will be described as an example. However, the same principle can be applied to other systems except the cone-beam computerized tomography system. Therefore, it will be obvious that the scope of the present invention defined by the appended claims can be applied to the other systems having the beam-stop array that is curved and moveable, to which the same principle is applied.

Components constituting the present invention, when necessary, may be used in a single body or be separated from one another to be used. Further, some components may be omitted.

Exemplary embodiments of the beam-stop array that is curved and moveable and the cone-beam computerized tomography system comprising the same according to the present invention will be described with reference to FIGS. 1 to 7. In the drawings, the thicknesses of lines, the sizes of components, or the like may be exaggerated for clarity and convenience of explanation. The following terms are terms which are defined based on functionality in the present invention. Since the meanings of these terms may vary depending on a user or operator's intension or a custom, the definitions of these terms should be determined based on the entire content of the present specification that describes the present invention.

Figure 1:
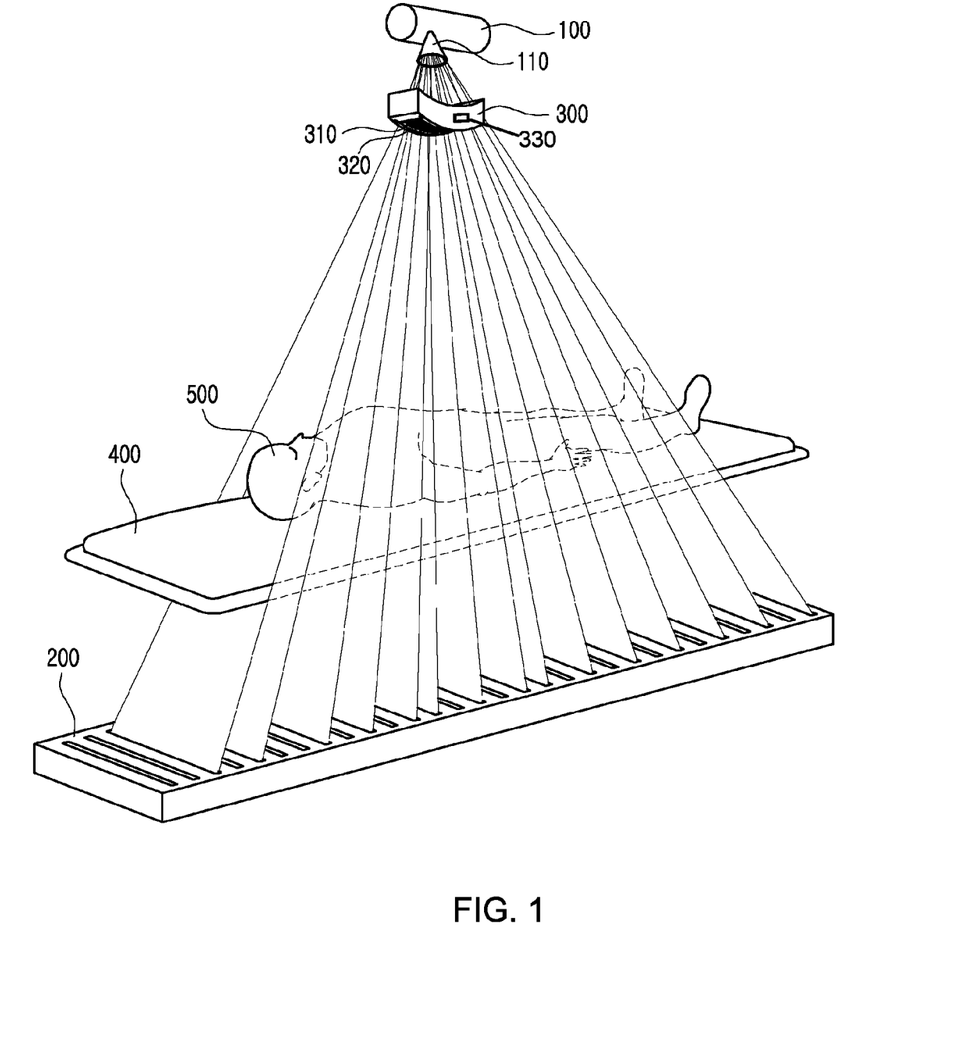
FIG. 1 is a perspective view illustrating a beam-stop array that is curved and moveable according to an embodiment of the present invention.
Figure 2:
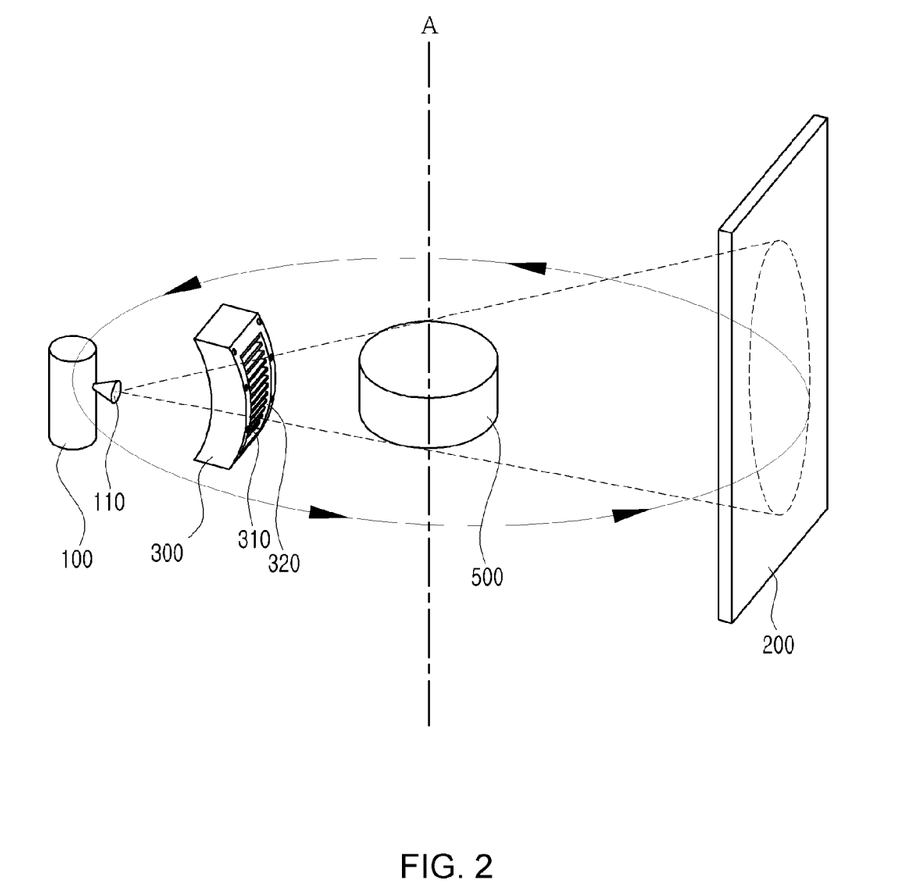
FIG. 2 is an entire schematic perspective view illustrating the beam-stop array according to the embodiment of the present invention.
Figure 3:
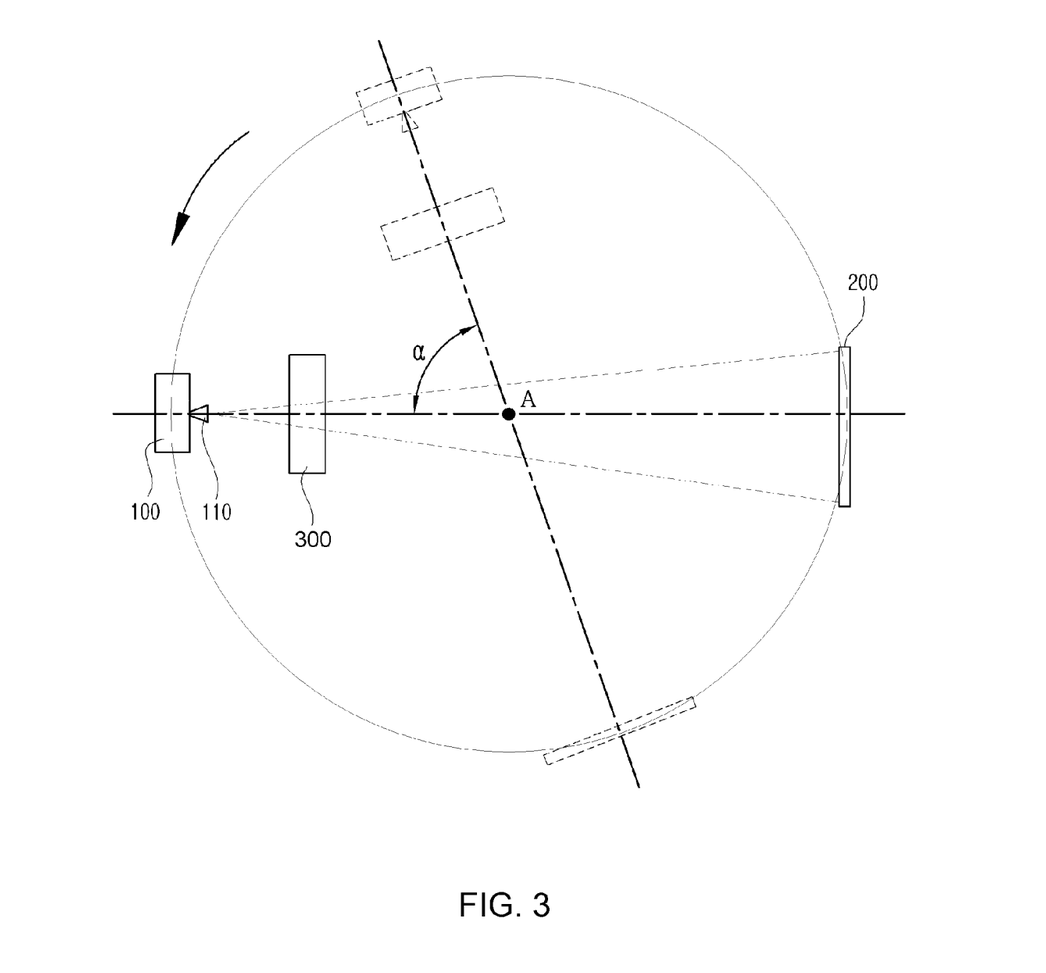
FIG. 3 is a plan view of FIG. 2.

Hereinafter, an embodiment of the entire configuration of the beam-stop array that is curved and moveable according to the present invention will be described with reference to FIGS. 1 to 3.

The beam-stop array according to the embodiment of the present invention comprises a generator 100, a flat panel detector 200 disposed facing the generator 100, a grid 300 that is curved and positioned between the flat panel detector 200 and the generator 100, a table 400 positioned between the grid 300 and the flat panel detector 200, and an object 500 positioned on the table 400. The beam-stop array may further comprise a controller 330 for controlling operations of the grid 300.

Generally, the term "gantry" is defined as a frame for accommodating the generator 100, the grid 300 and the flat panel detector 200. The term "gantry angle" refers to an angle that represents a degree where the gantry rotates about rotation axis A. The gantry angle is preferably measured as an angle corresponding to the distance where a focus 110 moves in an arc motion with respect to the rotation axis A.

The generator 100 generates radiation beams and rotates to a gantry angle about the rotation axis A. The radiation beams irradiated from the generator 100 are irradiated as cone-shaped beams with the focus 110 of the generator 100 as a vertex. Such a cone beam passes through the grid 300 and reaches the flat panel detector 200 via the object 500 on the table 400, and thereby the three-dimensional anatomical information of the object 500 may be obtained.

The grid 300 comprises a plurality of slits 310 spaced out at a predetermined distance from each other, and beam-stop units 320 that are alternately disposed with the plurality of slits 310, thereby stopping the radiation beams. Here, the plurality of slits 310 allow at least a portion of the radiation beams generated from the generator 100 to pass through. Preferably, the beam-stop units 320 further comprise a movable spaced unit 321 capable of changing the position of the plurality of slits 310 or the distance between the plurality of slits 310. Through the moveable spaced unit 321, the controller 330 may move the plurality of slits 310 by a predetermined space d corresponding to the plurality of slits 310 when the generator 100 moves by a predefined angle α (see FIGS. 4A and 4B). The length of the space d may be variously applied according to situations in which the beam-stop array is applied.

The table 400 positioned between the grid 300 and the flat panel detector 200 is preferably one that can move in a sliding motion. Accordingly, the photographing part of the object 500 positioned on the table 400 can be more efficiently controlled.

The grid 300 will be described in detail with reference to FIGS. 4A to 7.

The grid 300 has a curved shape and comprises the movable beam-stop units 320, so that, unlike a conventional flat-shaped grid, the image data of a wider area may be obtained as a more definite image. In a beam-stop array system using the flat-shaped grid, as the size of the object 500 onto which radiation beams are irradiated, i.e., the object 500, became larger, there was a limit in obtaining the required image data through photographing just once. This is because as the size of the object 500 increases, the degree of scattering of the radiation beams increases, and a penumbra forms, contaminating the image. In addition, as the photographing time increases, an indefinite image is generated due to the slight movement of the object 500.

Even when the irradiated radiation beams passing through the curved grid 300 are stopped by the beam-stop units 320, an unnecessary penumbra is not formed, due to its curved shape which is suitable for passing cone-beam-shaped radiation beams. In this state, the curved grid 300 is preferably formed to be curved convexly toward the table 400 so that the object 500 positioned so as to occupy a wide area on the table 400 may also be photographed.

The grid 300 according to the present invention may also change the position of the plurality of slits 310, so that it is possible to obtain sufficient image data for scatter correction through just one radiation scan. First, a process of obtaining image data for scatter correction will be briefly described with reference to FIG. 6.

Figure 6:
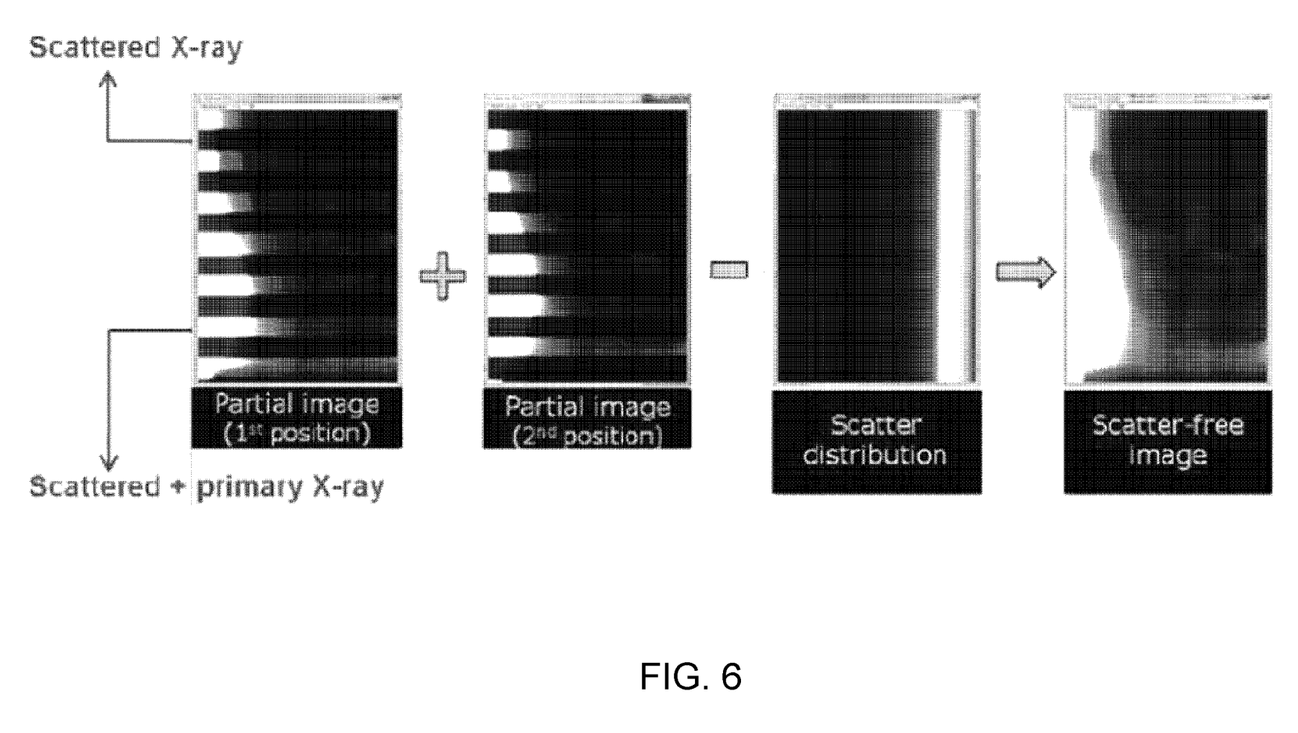
FIG. 6 shows images illustrating a process to which the beam-stop array is applied according to the embodiment of the present invention.

The plurality of slits 310 and the beam-stop units 320 are preferably formed perpendicular to the rotation axis A, and accordingly, images to be obtained are as shown in FIG. 6. Through the beam-stop units 320, only a portion of the irradiated radiation beams pass and may reach the flat panel detector 200. The portion where the irradiated radiation beams were unable to pass through the grid 300 appears dark in an image, so that the scattered radiation beams can be distinguished from the primary radiation beams irradiated from the generator 100. After only a portion of the object 500 is primarily photographed by the beam-stop unit 320, the plurality of slits 310 may be moved, and the object 500 may be secondarily photographed.

As the plurality of slits 310 move, images representing a plurality of different portions of the object 500 and the scattered parts on each image can be estimated. Thus, by finally combining the estimated images and scattered parts, a more accurate scatter distribution of the images may be obtained. When the scatter distribution is removed from the images, a definite image of the object 500 may be obtained.

The plurality of slits 310 are preferably controlled so that when the gantry moves by the predefined angle α, a plurality of different portions of the object 500 can be photographed by moving the plurality of slits 310 by the predetermined distance d corresponding to the plurality of slits 310 until before the gantry moves again. In this manner, it is possible to obtain a more definite image through a single scan. Further, the photographing time is also reduced, so that it is possible to reduce errors in images, caused by movement of the object 500.

There are several methods for changing the position of the plurality of slits 310, but two embodiments will be described.

Figure 4A:
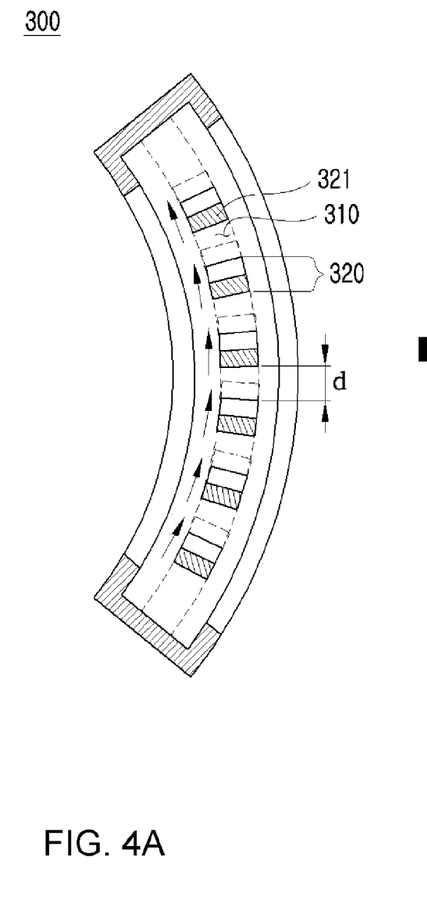
FIGS. 4A and 4B are a sectional views illustrating a beam-stop array according to the embodiment of the present invention.
Figure 4B:
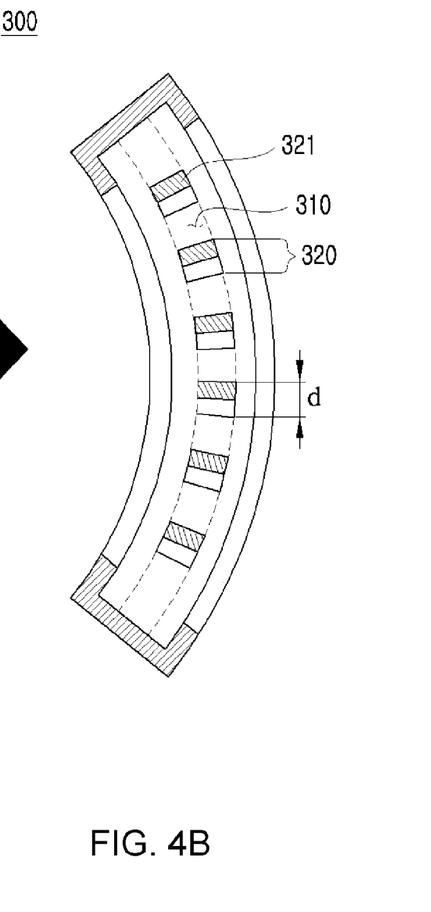

In an embodiment according to FIGS. 4A and 4B, the beam-stop units 320 further comprise the moveable spaced unit 321 that forms a portion thereof. The moveable spaced unit 321 vertically moves in the curved grid 300 by the controller 330, thereby changing the position of the plurality of slits 310.

Here, when the gantry angle moves by the predefined angle α, the moveable spaced unit 321 moves upward or downward by the predetermined distance d, so that the position of the plurality of slits 310 can be moved by the predetermined distance d in a state in which the space between the plurality of slits 310 is maintained. The predefined angle α and the predetermined distance d may be formed in various combinations. However, the predefined angle α and the predetermined distance d are preferably determined so that the entire image of the object 500 can be obtained through a single scan based on the gantry rotating once about the center axis A.

Figure 5A:
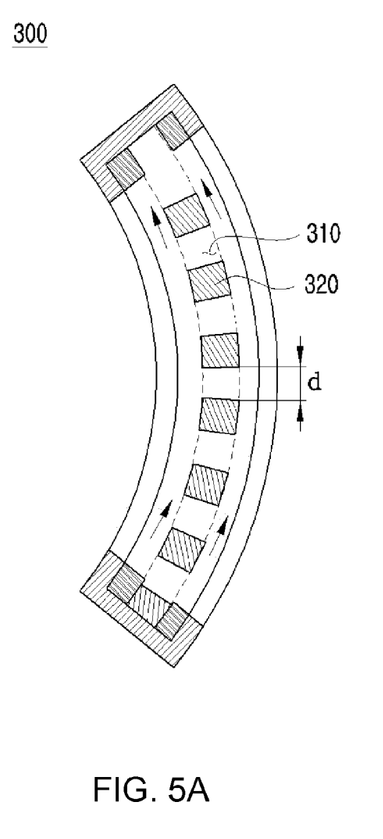
FIGS. 5A and 5B are a sectional views illustrating a beam-stop array according to a modification of the present invention.
Figure 5B:
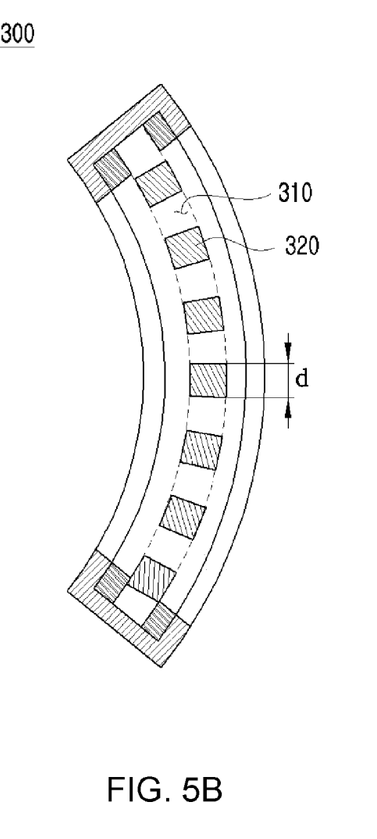

In another embodiment according to FIGS. 5A and 5B, the entire beam-stop units 320 positioned inside the grid 300 moves vertically, and the position of the plurality of slits 310 move together with the beam-stop units 320, accordingly. However, like the embodiment of FIGS. 4A and 4B, the predefined angle α and the predetermined distance d are preferably determined so that the entire image of the object 500 can be obtained through a single scan.

As the gantry rotates, the beam-stop units 320 positioned inside the grid 300 can be set to move automatically. Preferably, the beam-stop units 320 are vertically movable at a constant speed.

In order to obtain accurate scatter distribution, the beam-stop units 320 must have a function of being able to completely block the primary radiation beams. For such purposes, it is preferable that grid 300 is formed of lead having a thickness of 5 mm. In addition to the thickness, the width of the grid 300 acts as an important factor. In this case, in order to obtain more accurate data, the ratio of the thickness of a slit in the plurality of slits 310/the thickness of a beam-stop unit in the beam-stop units 320 is preferably 1.0.

The difference between the respective images obtained by the application of the conventional grid and by the application of the curved movable beam-stop array according to the embodiment of the present invention will be described in detail with reference to FIG. 7. Respectively, the upper left and right sides of FIG. 7 each represent images and a graph obtained through cone-beam computerized tomography scanning to which a flat grid is applied. The lower left and right sides of FIG. 7 respectively represent images and a graph, obtained by applying the curved grid 300 according to the present invention.

Figure 7:
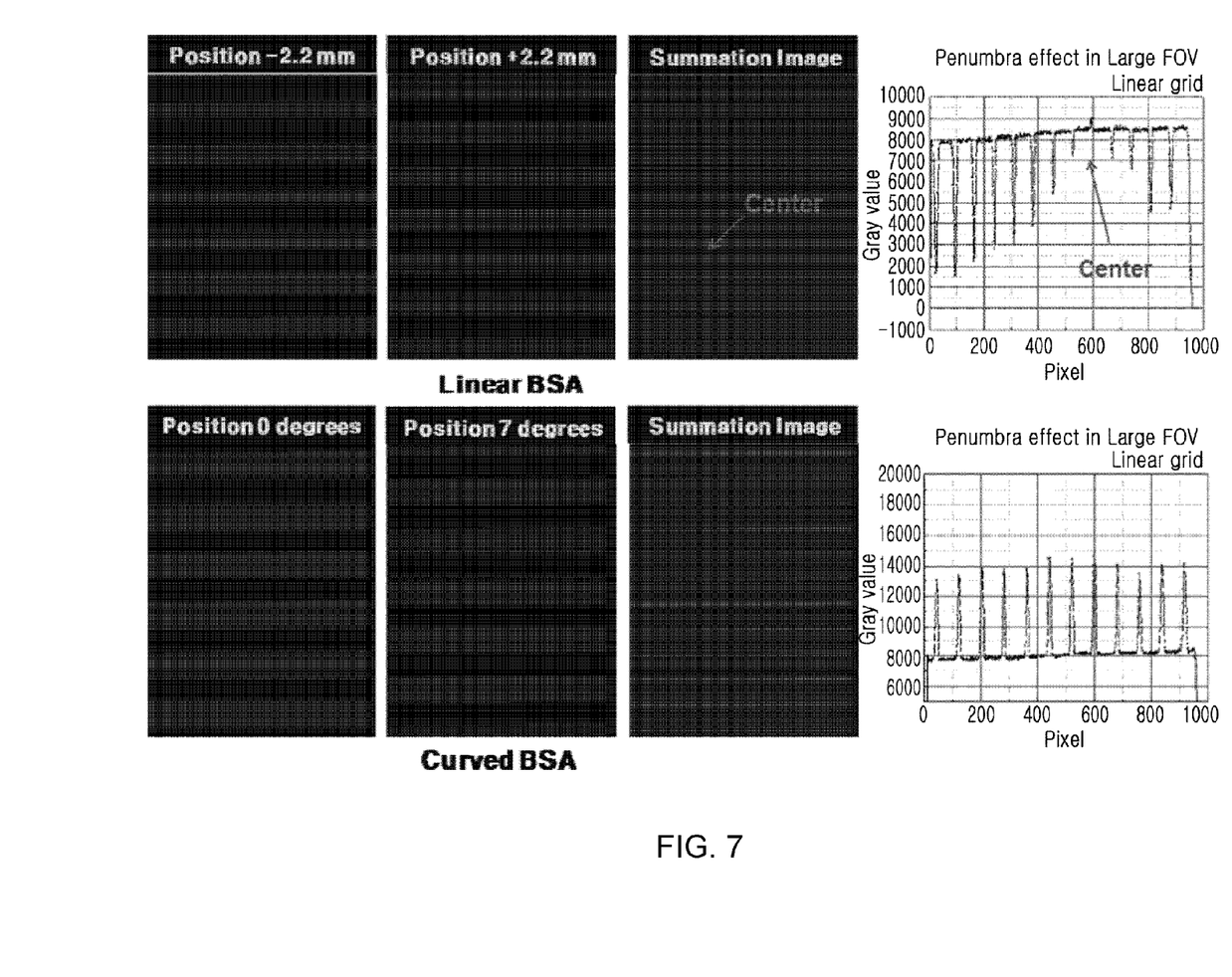
FIG. 7 shows images and graphs comparing and illustrating data respectively obtained by applying a conventional grid and the beam-stop array according to the embodiment of the present invention.

A phenomenon in which the penumbra area of the combination of the two images photographed using the flat grid gradually worsens with distance, is shown in the images on the upper left side of FIG. 7. Further, in the graph at the upper right side of FIG. 7, values corresponding to the gray values are drawn in an erratic form. Particularly, seeing that the change in gray value is miniscule in one section of the graph which corresponds to the middle point of the grid, it can be ascertained that a penumbra formed in this section, contaminating the image.

On the other hand, the images and graph at the lower left and right sides of FIG. 7 show a result arising when two images photographed using the curved grid 300 are combined, the penumbra area is constant without being influenced by distance.

As described above, the beam-stop array according to the present invention is easily attached to a radiation planning cone-beam computerized tomography system and a radiotherapy apparatus, to be used in identifying the position of a patient or tumor just before radiotherapy is performed. Further, the beam-stop array according to the present invention can be applied to various cone-beam computerized tomography systems used in a wide range of fields including plastic surgery, maxillofacial surgery, dental surgery, and the like, thereby obtaining high utilization of the beam-stop array.

The foregoing embodiments and advantages are merely exemplary and are not to be construed as limiting the present disclosure. The present teachings can be readily applied to other types of apparatuses. This description is intended to be illustrative, and not to limit the scope of the claims. Many alternatives, modifications, and variations will be apparent to those skilled in the art. The features, structures, methods, and other characteristics of the exemplary embodiments described herein may be combined in various ways to obtain additional and/or alternative exemplary embodiments.

As the present features may be embodied in several forms without departing from the characteristics thereof, it should also be understood that the above-described embodiments are not limited by any of the details of the foregoing description, unless otherwise specified, but rather should be construed broadly within its scope as defined in the appended claims, and therefore all changes and modifications that fall within the metes and bounds of the claims, or equivalents of such metes and bounds are therefore intended to be embraced by the appended claims.

What is claimed is:

1. A beam-stop array, comprising:
a generator configured to generate radiation beams while rotating to a gantry angle;
a grid being curved and positioned in a radiation direction of the radiation beams generated from the generator and being rotatable together with the generator; and
a controller controlling operations of the grid,
wherein the grid comprises a plurality of slits that are spaced movable within the grid and apart at a predetermined distance from each other, the plurality of slits allowing at least a portion of the radiation beams generated from the generator to pass through to enable a plurality of portions of an object to be imaged, and
wherein the controller moves the plurality of slits by a predetermined distance when the generator moves by a predefined angle, thereby enabling a plurality of different portions of the object to be imaged.

2. The beam-stop array of claim 1, further comprising a flat panel detector disposed facing the generator, and wherein the grid is positioned between the flat panel detector and the generator.

3. The beam-stop array of claim 2, wherein the generator and the grid rotate about a rotation axis, and wherein the grid is positioned between the generator and the object, and the plurality of slits are positioned perpendicular to the rotation axis.

4. The beam-stop array of claim 3, wherein the grid is curved convexly toward the object.

5. The beam-stop array of claim 1, wherein the grid further comprises a beam-stop unit which blocks radiation beams, being alternately disposed with the plurality of slits.

6. The beam-stop array of claim 5, wherein the beam-stop unit comprises a movable spaced unit.

7. The beam-stop array of claim 6, wherein the controller controls a movement of the movable spaced unit.

8. The beam-stop array of claim 6, wherein the movable spaced unit comprises a plurality of spaced units to stop at least a portion of said plurality of slits.

9. The beam-stop array of claim 1, wherein a ratio of a space between two adjacent slits of the plurality of slits to a thickness of the grid is 1.0.

10. A cone-beam computerized tomography system comprising the beam-stop array of claim 1, wherein the controller moves the plurality of slits by the predetermined distance after a first image of the object is obtained, and the first image is obtained when the generator rotates by the predefined angle.

* * * * *